United States Patent [19]

Higashiizumi et al.

[11] Patent Number: 5,129,398
[45] Date of Patent: Jul. 14, 1992

[54] ULTRASONIC DIAGNOSTIC DEVICE

[75] Inventors: Takao Higashiizumi; Kazushige Imabeppu, both of Tokyo, Japan

[73] Assignee: Yokogawa Medical Systems, Limited, Tokyo, Japan

[21] Appl. No.: 476,501

[22] PCT Filed: Dec. 10, 1988

[86] PCT No.: PCT/JP88/01254
§ 371 Date: Jun. 8, 1990
§ 102(e) Date: Jun. 8, 1990

[87] PCT Pub. No.: WO89/05122
PCT Pub. Date: Jun. 15, 1989

[30] Foreign Application Priority Data

Dec. 11, 1987 [JP] Japan .................. 62-314897

[51] Int. Cl.⁵ .................................................. A61B 8/00
[52] U.S. Cl. .......................... 128/660.01; 128/660.07; 128/661.01; 73/625
[58] Field of Search ............... 128/660.01, 661.01, 128/662.03, 661.03, 660.07; 73/625

[56] References Cited

U.S. PATENT DOCUMENTS

| | | | |
|---|---|---|---|
| 4,140,107 | 2/1979 | Lancée et al. | 128/660.07 |
| 4,412,147 | 10/1983 | Nagura et al. | 128/660.07 |
| 4,763,661 | 8/1988 | Sommer et al. | 128/600.07 |
| 4,781,199 | 11/1988 | Hirama et al. | 128/660.01 |
| 4,821,574 | 4/1989 | Takamizawa | 128/661.01 |
| 4,821,706 | 4/1989 | Scheicher et al. | 128/660.01 |
| 4,870,971 | 10/1989 | Russell et al. | 128/661.01 |

Primary Examiner—Francis Jaworski
Assistant Examiner—George Manuel
Attorney, Agent, or Firm—Moonray Kojima

[57] ABSTRACT

An ultrasonic diagnostic device according to the present invention in which a driving mechanism for driving vibrators in an opening port for the transmission of ultrasonic waves with weighting can be the one of low cost and low heat loss is characterized in that a plurality of driving signals for driving a plurality of vibrators in an opening port for the transmission of ultrasonic waves are made to have different waveforms from each other for weighting.

3 Claims, 2 Drawing Sheets

ULTRASONIC DIAGNOSTIC DEVICE

TECHNICAL FIELD

The present invention relates to the improvement of an ultrasonic diagnostic device which performs a linear scan. To be precise, it relates to the improvement of a mechanism for driving a plurality of vibrators being concerned in the transmission of an ultrasonic beam with a weighted method.

BACKGROUND ART

As commonly known, in an ultra sonic diagnostic device for medical use provided with an ultra sonic probe comprising minute vibrator groups in an array-form, the scan of an ultrasonic beam is electronically performed. As a device of this kind, an ultrasonic diagnostic device which displays an M mode image as well as a B mode image with a linear scan is actually used.

FIG. 4 is an illustrative representation of a scanning method with which both of these mode images can be obtained. In FIG. 4, minute vibrators 1, 2, . . . 26 are disposed in an array-form. Each of these vibrators is connected to a transmission and reception circuit, not shown in the drawing, through a changeover switch. The minute vibrators, for example, forming groups of 1-5, 2-6, 3-7, 4-8, successively form an opening port for transmitting and receiving ultrasonic waves to perform a scan with the operation of the changeover switch. In other words, the linear scan is executed forming ultrasonic beams (1), (2), (3) and (4) by moving the opening port pitch by pitch in the direction in which the minute vibrators are disposed, and echo signals in individual pitches are collected. After the transmission and reception of the ultrasonic beam (4), the transmission and reception of an ultrasonic beam (5) are performed by a group of minute vibrators 21 to 25, and in this beam position the transmission and reception in a M mode is performed. In the similar way to the above, a linear scan by the groups of minute vibrators 5-9, . . . 8-12 is performed and the transmission and reception in a M mode is performed by the groups of minute vibrators 21-25, and echo signals in individual pitches are collected. In executing the scan as mentioned above, the imaging of a B mode image or an M mode image of a desired portion can be performed.

In the past, an ultrasonic diagnostic device having such functions as mentioned above is so constituted that a transmission driver with a high voltage control mechanism is provided to each of these vibrators, and a pulse signal from a transmission pulse generator is supplied to the transmission driver for driving a vibrator with a high voltage. In this case, among a plurality of vibrators which constitute an opening port, a vibrator positioned in the center is given the highest voltage, for example, 100 V and a voltage to be given to a vibrator is decreased in proportion to the increase in the distance from the center to the position of a vibrator so that a weighted driving can be performed. Weighting of driving is performed by controlling a high voltage, which is given to each transmission driver as a power supply, with a high voltage control mechanism. In such a case, a high voltage needs a very high speed control such as the change from 0 V to 100 V in 10 μsec to correspond the changeover of the opening port in a linear scan or the changeover between a B mode and an M mode. It causes high cost to have a plurality of transmission drivers with such high speed high voltage control mechanisms. There is also a problem that a high voltage control mechanism produces large quantity of heat because when the voltage is lowered it absorbs a surplus voltage.

SUMMARY OF THE INVENTION

An object of the present invention is to provide an ultrasonic diagnostic device having a driving mechanism of low cost and low heat loss for driving the vibrators in an opening port for ultrasonic waves with a weighted method.

An ultrasonic diagnostic device according to the present invention is characterized in that the weighting of a plurality of signals for driving the individual ultrasonic vibrators in an opening port for ultrasonic waves is executed by making each of these signals have a different waveform from each other.

BEST MODE FOR CARRYING OUT THE INVENTION

Figure 1:
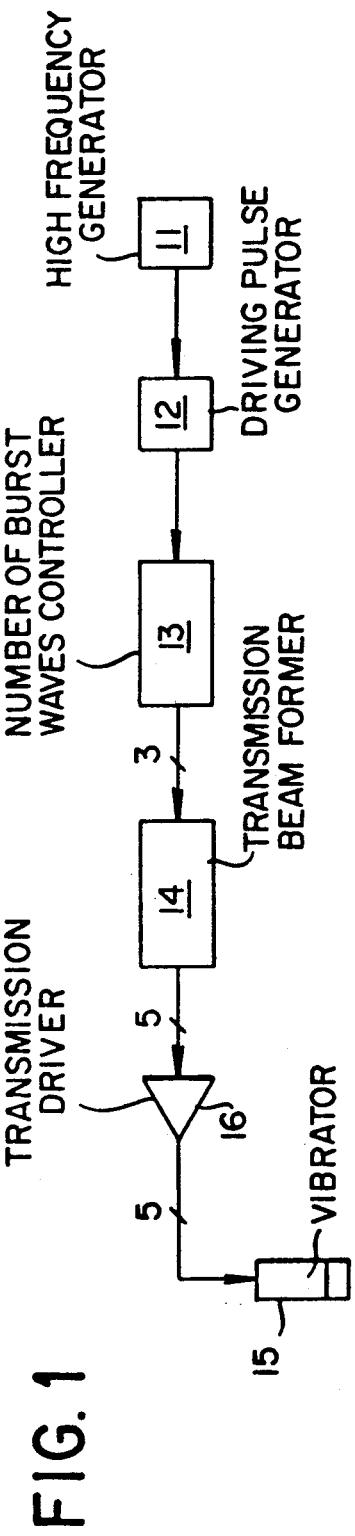
FIG. 1 is a block diagram showing an embodiment of the present invention.
Figure 2:
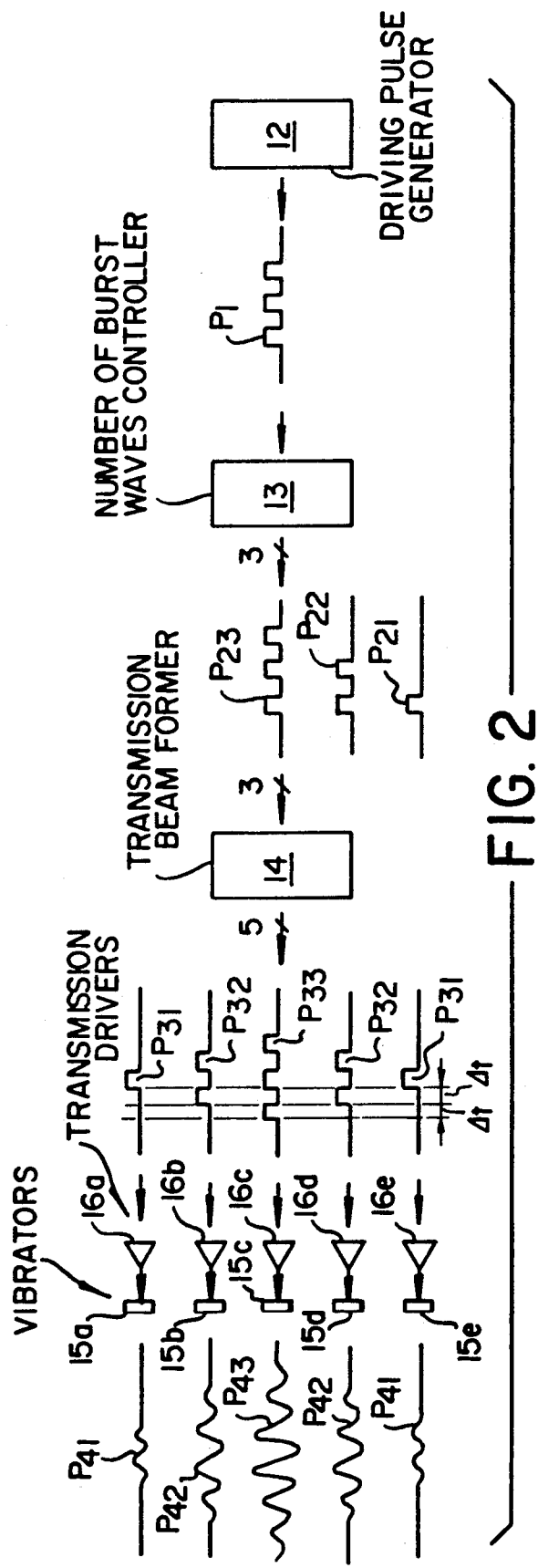
FIG. 2 is an illustrative representation of the operation of an embodiment according to the present invention.

The detailed explanation on a device according to the present invention will be given in the following referring to the drawings. FIG. 1 is a block diagram showing an embodiment according to the present invention; it shows a principal part of a transmission system. In the FIG. 1, the transmission system is constituted with the following: a high frequency oscillator 11 for generating a high frequency signal; a driving pulse generator 12 for generating driving pulses for burst waves based on the high frequency signal from the high frequency generator 11; a number of burst waves controller 13 for forming a plurality of driving pulses having different number of burst waves from each other based on the input driving pulses; a transmission beam former 14 for giving specified delay quantities between a plurality of driving pulses from the number of burst waves controller 13; and a transmission driver 16 for generating a plurality of high voltage pulses for driving vibrators 15 based on a plurality of driving pulses from the transmission beam former 14. In this case, it is assumed that the transmission and reception of ultrasonic waves for one time is, for example as shown in FIG. 2, performed using an opening port constituted with 5 vibrators 15a, 15b, 15c, 15d and 15e; a linear scan is performed by successively moving such an opening port. Transmission drivers 16a, 16b, 16c, 16d and 16e provided corresponding to individual vibrators are respectively connected to the corresponding vibrators.

Figure 3:
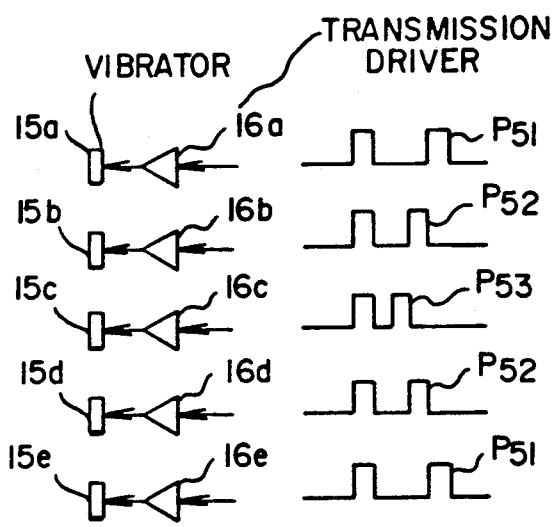
FIG. 3 is an illustrative representation of the operation of another embodiment according to the present invention.
Figure 4:
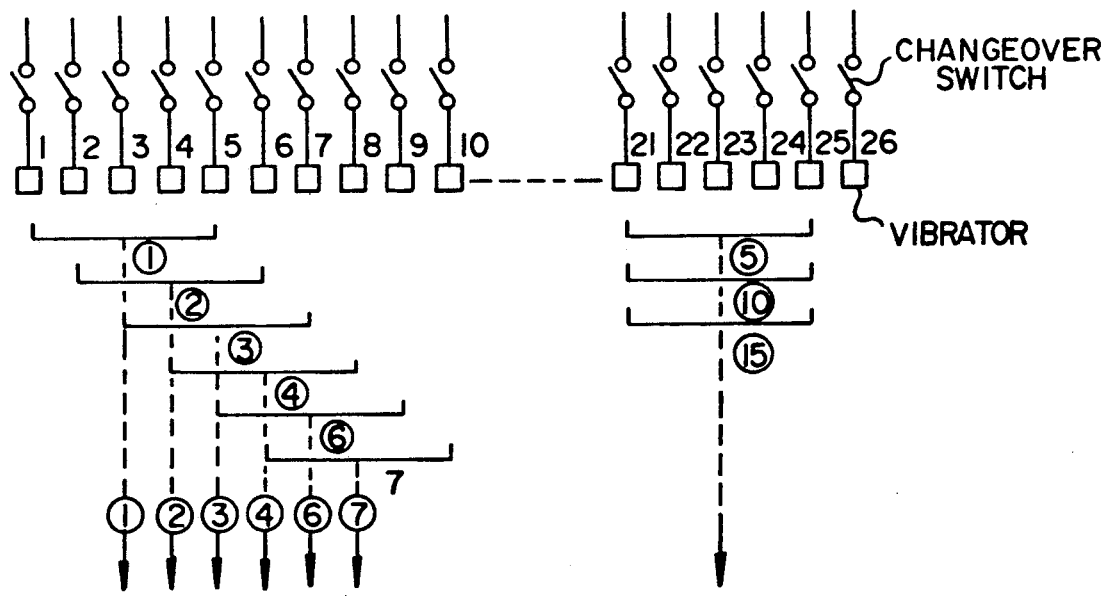
FIG. 4 is an illustrative representation of a scanning method for obtaining a B mode image and an M mode image.

Next, the operation of a transmission system constituted as mentioned in the above will be explained in the following. FIG. 2 is an illustrative representation of the operation of one ultrasonic beam, and the individual symbols in the figure are used in the same meaning as in the above case. The driving pulse generator 12 gener-"

ates, for example, driving pulses P1, each having 3 burst waves, based on the high frequency signal from the high frequency oscillator 11, and they are input to the number of burst waves controller 13. The number of burst waves of the driving pulses generated by the driving pulse generator 12 is not limited to 3. The number of burst waves controller 13 forms 3 kinds of driving pulses P21, P22 and P23 having the same amplitude and the number of burst waves of 1, 2 and 3 respectively from the driving pulses P1. The transmission beam former 14 forms a driving pulse P33, two driving pulses P32 delayed from P33 by $\Delta t$, and two driving pulses P31 further delayed by $\Delta t$, based on the driving pulses P23, P22 and P21. The driving pulse P33 is input to the transmission drive 16c corresponding to the center vibrator in an opening port, the driving pulses P32 are input to the transmission drivers 16b and 16d corresponding to the vibrators positioned adjacent to the center vibrator on both sides, and the driving pulses P31 are input to the transmission drivers 16a and 16e corresponding to the vibrators positioned in both end parts of the opening port. Therefore, the vibrator 15c positioned at the center of the opening port is driven by a driving pulse having the largest number of burst waves and the earliest timing. The other vibrators are driven by driving pulses having less number of burst waves and later timings in proportion to the distances from the center of the opening port to the positions of vibrators. Thereby, from the vibrators 15a, 15b, 15c, 15d and 15e ultrasonic waves P41, P42, P43, P42 and P41 are respectively transmitted at the timings as shown in the figure. In this case, even if the widths of pulses driving vibrators are the same, with the increase in the number of burst waves, the intensity of output ultrasonic waves becomes stronger, so that the strongest ultrasonic waves are output from the vibrator at the center of the opening port, and from the vibrators positioned closer to the end parts ultrasonic waves of weaker intensity are output. In other words, the weighting of ultrasonic waves to be transmitted is realized. Besides the control of the number of burst waves as mentioned in the above, another weighting method can be considered in which, for example as shown in FIG. 3, the vibrator 15c positioned at the center of the opening port is driven by driving pulses P53 having the frequency closest to the center frequency of the vibrator 15c, and other vibrators are driven by driving pulses P52 and P51 having frequencies which are deviated by degrees from the center frequency. In any event, the weighting of transmission waves is performed using driving signals, each of them having a different waveform from each other, for driving a plurality of vibrators forming an opening port.

When the weighting of transmission of ultrasonic waves is performed with the method as mentioned above, a high voltage power supply to be given to transmission drivers can be a constant voltage power supply regardless of the weighting; it is not needed to be the one having a high speed voltage control mechanism; therefore, a transmission system can be constituted at low cost; and since there is no need for it to generate a variable voltage, it is made possible to manufacture a mechanism of low heat loss.

While there has been given the explanation on another best mode for carrying out the present invention, it will be understood that various modifications may be easily made within the true spirit and scope of the invention by persons having ordinary knowledge in the technical field to which the invention belongs.

We claim:

1. In an ultrasonic diagnostic device comprising in an ultrasonic probe a plurality of vibrators disposed in an array and forming an opening port, the improvement comprising driving means for driving concurrently said plurality of vibrators forming said opening port to produce ultrasonic waves, said driving means comprising means for generating and weighting a plurality of driving signals to form different weighted waveforms that drive the plurality of vibrators to produce respectively different powers of ultrasonic waves.

2. The device of claim 1, wherein said driving means comprises means for applying to a vibrator located at a center of said opening port a driving signal having a maximum number of burst waves, and for applying to vibrators located away from said center of said opening port driving signals having a fewer number of burst waves.

3. The device of claim 1, wherein said driving means comprises means for applying to a vibrator located at a center of said opening port a driving signal having a predetermined frequency, and for applying to vibrators located away from said center of said opening port driving signals having frequencies which are deviated from said predetermined frequency.

* * * * *